United States Patent
Mann et al.

(10) Patent No.: US 8,845,903 B2
(45) Date of Patent: Sep. 30, 2014

(54) CHROMATOGRAPHY COLUMN METHOD OF VARIABLE SPEED OPERATION

(76) Inventors: William H. Mann, Chattanooga, TN (US); Mickey Mann, Chattanooga, TN (US)

(*) Notice: Subject to any disclaimer, the term of this patent is extended or adjusted under 35 U.S.C. 154(b) by 1364 days.

(21) Appl. No.: 12/246,658

(22) Filed: Oct. 7, 2008

(65) Prior Publication Data

US 2010/0084341 A1    Apr. 8, 2010

(51) Int. Cl.
*B01D 15/20* (2006.01)
*G01N 30/56* (2006.01)
*G01N 30/32* (2006.01)
*G01N 30/52* (2006.01)

(52) U.S. Cl.
CPC .......... *G01N 30/56* (2013.01); *G01N 2030/522* (2013.01); *G01N 2030/565* (2013.01); *B01D 15/206* (2013.01); *G01N 30/32* (2013.01)
USPC ........................................ 210/656; 210/198.2

(58) Field of Classification Search
CPC .................. B01D 15/206; G01N 30/32; G01N 2030/565; G01N 2030/522
USPC ........... 210/198.2, 635, 656, 659, 143; 95/82; 96/101
See application file for complete search history.

(56) References Cited

U.S. PATENT DOCUMENTS

| | | | | |
|---|---|---|---|---|
| 3,809,182 | A * | 5/1974 | Wilson | 182/148 |
| 3,966,609 | A * | 6/1976 | Godbille et al. | 210/198.2 |
| 4,597,866 | A * | 7/1986 | Couillard | 210/198.2 |
| 5,242,586 | A * | 9/1993 | Ransohoff | 210/198.2 |
| 6,190,560 | B1 * | 2/2001 | Mann | 210/656 |
| 6,736,974 | B1 * | 5/2004 | Mann | 210/656 |
| 6,843,918 | B2 * | 1/2005 | Hauck et al. | 210/656 |
| 7,132,053 | B2 * | 11/2006 | Hauck et al. | 210/656 |
| 7,435,350 | B2 * | 10/2008 | Noyes et al. | 210/656 |
| 2004/0177610 | A1 * | 9/2004 | Hendrickson | 60/489 |
| 2006/0219616 | A1 * | 10/2006 | Noyes et al. | 210/198.2 |
| 2007/0074510 | A1 * | 4/2007 | VerKuilen et al. | 60/422 |
| 2007/0090035 | A1 * | 4/2007 | Rahn et al. | 210/198.2 |
| 2007/0137338 | A1 * | 6/2007 | Nishi et al. | 74/335 |
| 2007/0144955 | A1 * | 6/2007 | Mann et al. | 210/198.2 |

* cited by examiner

*Primary Examiner* — Ernest G Therkorn
(74) *Attorney, Agent, or Firm* — Stephen J. Stark; Miller & Martin PLLC

(57) ABSTRACT

A chromatography column is normally filled with a slurry of media for operation. A piston normally compacts the slurry in the column. The piston moves through a cavity in communication with both a slurry inlet and slurry ports which are in communication with the interior of the chromatography column. A controller is configured to automatically adjust piston speeds along elevation zones of operation. Furthermore, presetting specific speeds less the maximum speed can be accomplished with the controller. A pressure sensor may also be employed to assist in switching speed of operation of the piston under particular pressure events.

11 Claims, 2 Drawing Sheets

CHROMATOGRAPHY COLUMN METHOD OF VARIABLE SPEED OPERATION

BACKGROUND OF THE INVENTION

1. Field of the Invention

The present invention relates an apparatus and method of operating a chromatography column and, more particularly, to such a chromatography column and a method for effectively packing media and/or automatically moving the top flow adapter at at least one predetermined speed less than a maximum speed and/or providing at least one programmably set bottom limit stop.

2. Description of Related Art

Chromatography is a process of separating components of a mixture of chemical substances through the percolation of fluid through a body or bed of comminuted or porous rigid material, known as media. In the process, the various component are often resolved, or separated, by their selective retardation as they are transported through the bed by a moving fluid or buffer. A solution of the substances to be separated becomes the moving phase of the system passing through the interstices in the stationary or continuous phase which are finely divided particles, possibly in the form of a gel slurry.

The substances in the moving phase are normally poured into the top of a chromatography column filled with the finely divided material, i.e., the media, that can absorb differentially the substances to be separated. The particular material used for the media varies widely with the substances to be separated. As the solution percolates down the column the components are separated from the buffer fluid which may be pumped back into the top of the column so as to again pass down through the bed as a carrier. The different substances as they travel down the column at different rates form bands of the different substances which are individually collected at the outlet.

A chromatography column typically comprises a hollow vertically disposed cylindrical housing including a liquid dispensing section, also referred to as a top flow adapter or plunger in many embodiments, at the upper end and through which the buffer and substances to be separated are dispensed to the media bed, and a liquid collecting section at the lower end for collecting the substances and buffer individually. The media or bed through which the buffer fluid and mixture to be separated and purified percolates is located between these sections. The liquid dispensing section and liquid collecting section may each include a respective distribution plate and at least one of the plates may be connected in an assembly with an axially movable plunger-like body positioned within the housing. After the column is charged with the bed media, the plunger body is often forced toward the bottom to compress or pressurize the media bed which has been poured into the column.

Prior art designs have allowed for the plunger to be moved with hydraulics manually controlled by an operator such as those shown and described in Applicant's U.S. Pat. No. 6,736,974, incorporated herein by reference. When the operator manually actuated the hydraulic controls of the prior art design, he or she would cause valves to open and shut to move the plunger up or down at a single, or maximum speed. In order to change the speed of operation of the plunger, in a prior art device, air pressure provided to a hydraulic pump could be varied manually with a regulator on the air supply. However, this process was completely operator dependent and not particularly precise. If left to normal operation with the controller, the only speed of operation was the maximum speed.

The prior art packing technique involved an operator lowering a plunger until it stopped. When lowering the plunger at its single fastest speed, when the liquid in the column was first encountered, the plunger could continue downward at this speed thereby likely continuing to pack the bed. This could lead to an undesirable pack in at least some situations.

Accordingly, a need exists to improve the operational methods by providing an improved chromatography column.

SUMMARY OF THE INVENTION

The present invention recognizes and addresses these needs and others.

Consequently, it is an object of at least one embodiment of the present invention to provide an improved chromatography column and method of its operation.

It is another object of at least one embodiment of the present invention to provide a chromatography column capable of automatically changing plunger speeds according to predetermined settings.

It is another object of at least one embodiment of the present invention to provide a chromatography column with a controller which can move the top flow adapter at least two programmably selected and/or predetermined speeds.

Accordingly, the present invention provides a chromatography column having a cylinder defining a cavity for containing media therein. A top flow adapter or plunger is operatively coupled to a hydraulic piston moveable through at least a portion of the cavity within the cylinder during operation. A base is normally connected to the cylinder. The plunger may be operatively coupled to the hydraulic piston to adjust the height of the plunger above the base to provide a desired resin height between the plunger and the base for operation. The plunger may also be utilized to exert a force on the resin to "pack" the resin in the column.

A controller is also provided which preferably at least assists in providing one of a number of operational capabilities not provided in the prior art. The controller receives an input relative to at least one of three of the hydraulic cylinders utilized in the preferred embodiment relating to at least one of position and/or pressure. These inputs can be utilized to move the top flow adapter relative to the column of at least two predetermined speed settings such as could be set to occur at a particular plunger elevation, to switch to a slower speed upon encountering a predetermined pressure or pressure differential pressure at each of at least some of the pistons, and/or to prevent the top flow adapter from contracting a manual step in such an embodiment.

The hydraulic system preferably includes at least one piston which is driven by at least one hydraulic cylinder. In the preferred embodiment, a plurality of hydraulic cylinders are utilized which are driven from a common hydraulic pressure source which is coupled to a controller through a proportional servo valve. The controller receives feedback related to each of the cylinders for increased performance capabilities. Upon receipt of a signal from a controller, the hydraulic cylinder(s) drive the hydraulic piston(s) at a programmable speed at maximum speed or slower. Depending upon the configuration of the column, the piston(s) drive the plunger and/or the cylinder upwardly or downwardly.

BRIEF DESCRIPTION OF THE DRAWINGS

The particular features and advantages of the invention as well as other objects will become apparent from the following description taken in connection with the accompanying drawings in which.

DETAILED DESCRIPTION OF THE PREFERRED EMBODIMENTS

Figure 1:
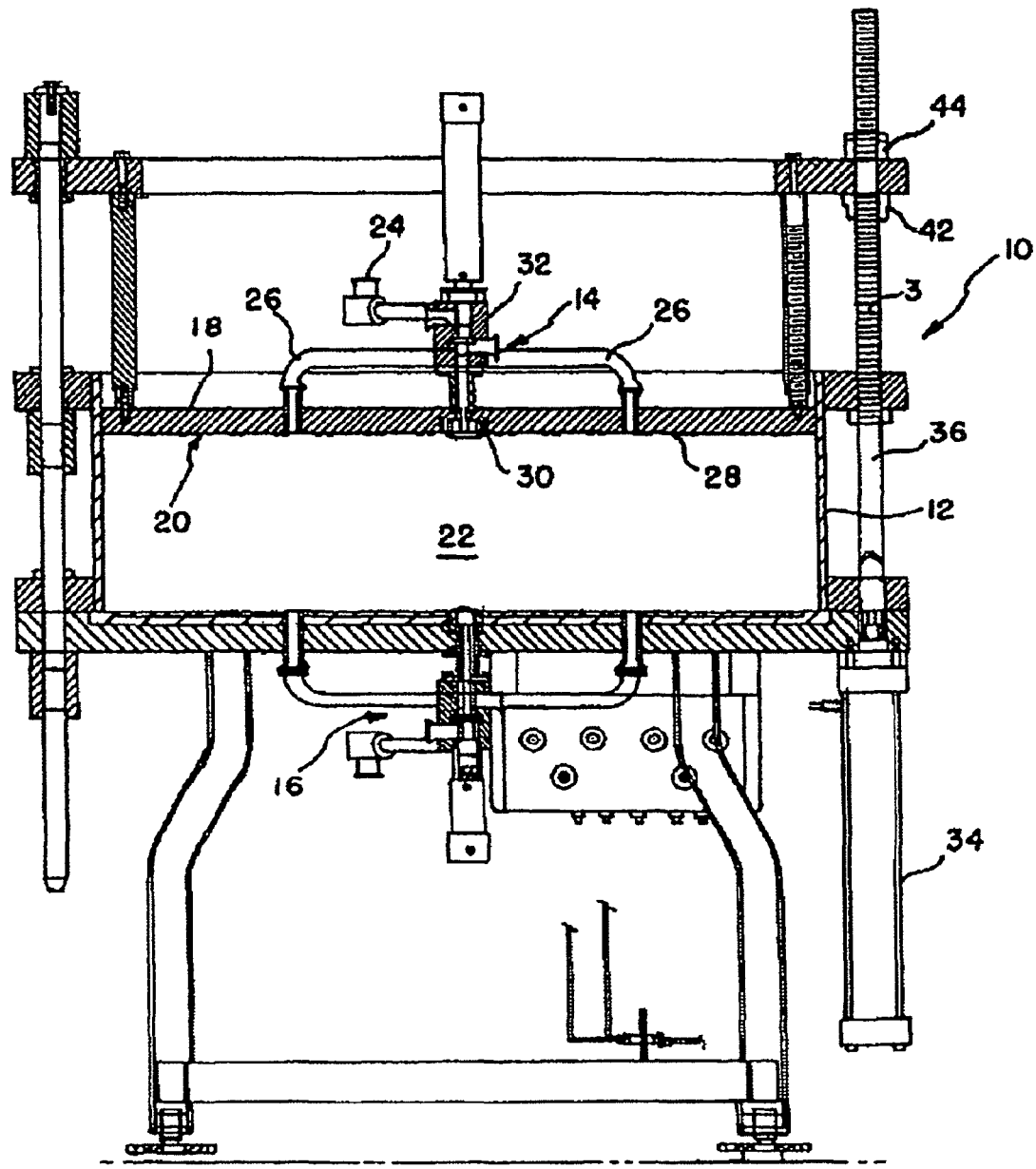
FIG. 1 is a side plan view of a chromatography column according to the present invention in a first operational position.
Figure 2:
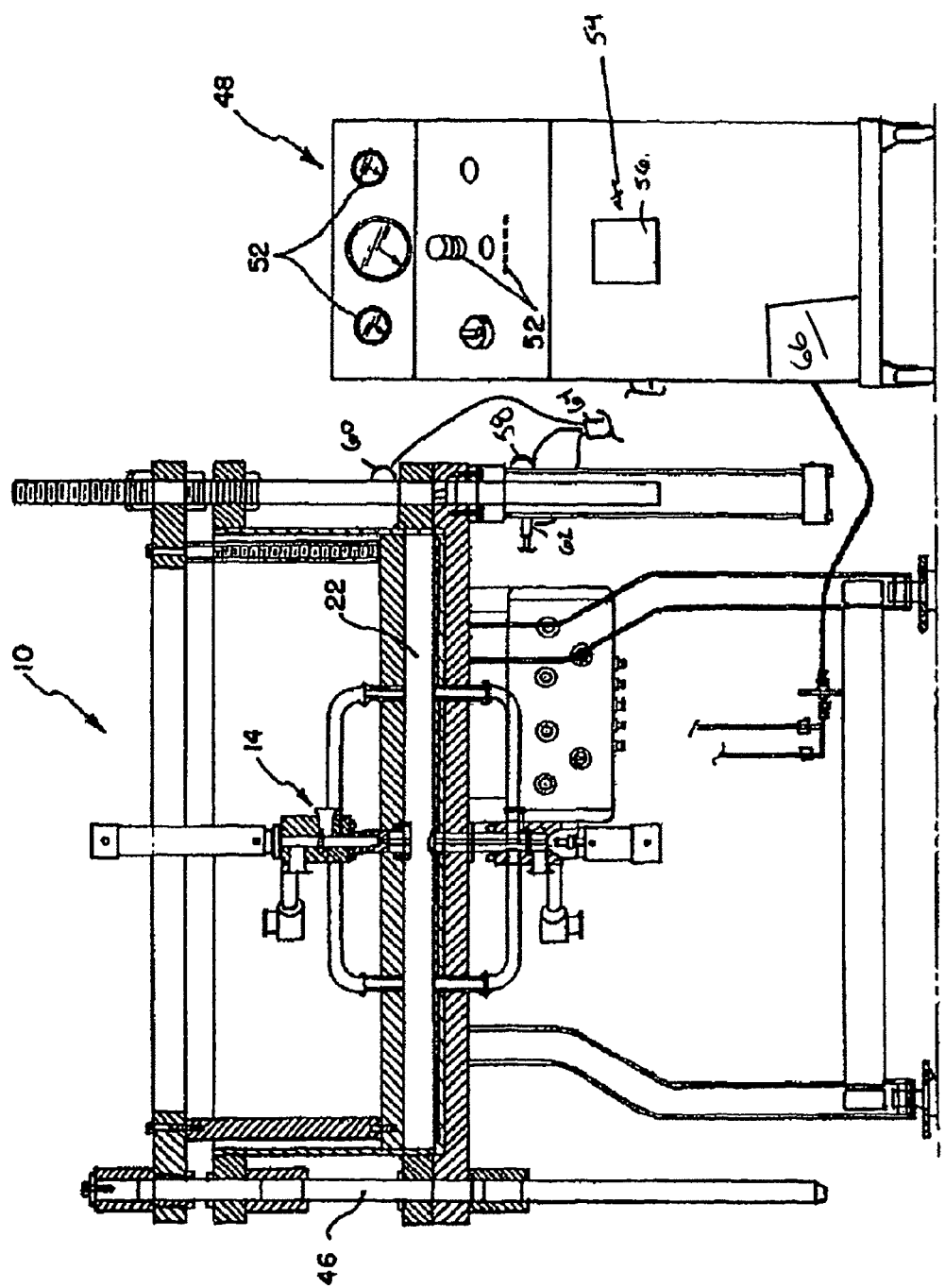
FIG. 2 is a side plan view of the chromatography column illustrated in FIG. 1 in a second operational position.

The present invention is concerned with a method and apparatus for permitting maintenance within a chromatography column which houses a slurry and/or media during operation. FIGS. 1-2 depict one such chromatography column 10 with the slurry removed. The column 10 comprises an elongated hollow cylindrical housing 12, or cylinder, having a dispersion section 14 at the top and a collecting section 16 at the bottom. The dispersion section 14 includes a cylindrical drum 18 having an upper cylindrical plunger head 20 formed at the lower end. The plunger 20 or top flow adapter is normally disposed within the upper portion of the housing 12 such as illustrated in the first operational position of FIG. 1. The plunger 20 may also be moved, such as with a drive system similar to the hydraulic arrangement illustrated to the second operational position of FIG. 2. The movement of the head 20 allows for the compression of media to "pack" resin and/or for the use of a particularly sized media column with the cavity 22 formed between the dispersion and collection sections 14, 16 and/or between the plunger 20 and the base 64.

The dispersion section 14 may also include a product inlet 24 along with an inlet manifold 26 to distribute incoming fluid throughout a top portion of a resin column contained within the cavity 22. An inlet screen 28 may be connected to the plunger head 20 by connectors such as TEFLON™ snaps (not illustrated) and/or an inner clamp nut 30. The distributor plate 31 may be removable as well. A discussion of a distributor plate 31 design may be found in U.S. Pat. No. 6,190,560. A slurry fill valve 32 such as the valve taught in co-owned U.S. Pat. No. 6,190,560 may also be connected to the plunger head 20 and/or dispersion section 14. The slurry fill valve 32 provides a way to fill the cavity 22 with resin without the need to lift the plunger 28 out of the cavity 22 within the cylinder 12. Although a preferred dispersion section 14 is described, other dispersion sections designs could be utilized as well.

In order to move the plunger head 20 in an operational mode from the first operational position shown in FIG. 1 to the second operational position of FIG. 2, a drive system, illustrated as a hydraulic system is preferably utilized. Other systems, such as electric or pneumatic may be appropriate drive systems in other embodiments.

The drive system is comprised of at least one, and preferably three or more, drive cylinders 34. The drive cylinders 34 move drive pistons 36 which are coupled to the drum 18. In the preferred embodiment, a portion of the drive pistons is a threaded portion 38 to allow for the drive piston 36 to connect or couple to connection arms 40 at specific locations relative to the drive piston 36 such as with nuts 42, 44. Guide rods 46 may be utilized in addition to the drive system to ensure linear movement of the drum 18 and plunger 20 within the cavity 22 of the cylinder 12.

The drive system also includes a control unit 48 which may be operated to control movement of the plunger 20. The control unit preferably has a hydraulic engine which provides fluid under pressure to operate the drive cylinders 34 or may be connected to a hydraulic supply. Controls 50 allow an operator to direct the movement of the plunger 20 within the cylinder 12. Controls 50 may allow for operation of the hydraulic engine, or pump, a float switch, direction of movement selection and/or controlling valves. Gauges 52 allow for the operating parameters to be monitored. Gauges 52 may monitor air pressure, column pressure and/or drive system pressure, such as hydraulic pressure.

The control unit 48 is also preferably equipped with a controller which is a hydraulic control unit (HCU) 54. The HCU 54 is preferably equipped with a touch screen 56 for operation of at least certain functions of the HCU 54. As discussed below, some of the operations which can be performed and or assisted by the HCU 54 include the movement of the top flow adapter through the movement of the plunger 20 down and possibly up at a plurality of predetermined speeds including first and second speeds, stopping movement of the plunger at a bottom limit, and/or movement of the plunger at programmed speeds such as in a pack process as will be discussed in further detail below. It will be understood to one of ordinary skill in the art that as the plunger 20 moves, so does the top flow adapter in the preferred embodiment.

The column 10, like that disclosed in co-owned U.S. Pat. No. 7,402,251, incorporated herein by reference, preferably utilizes sensors which provide input to the HCU 54 which can then vary signals to control operation of certain procedures in an improved manner as will be discussed below. The cylinders 34 may have sensors 58 in communication therewith which can sense a pressure relative to column pressure. Sensors 58 provide an output which is received by the HCU 56 in the preferred embodiment. Sensors 60 which sense position of the plunger 20 either directly or indirectly are also employed which provide a position relative to each of the pistons 36. Output from sensors 60 is also provided to the HCU 54.

Position sensors 60 in cooperation with the HCU 54 provide various capabilities which have not been achievable with prior art designs. First, height ranges of the plunger 20 can have preset speeds of operation. The height ranges and settings related to speeds may be programmed by the operator.

In an operational mode, the operator may utilize a touch screen 56, or other input device, to input a predetermined or programmed speed of the plunger 20 at or less than a maximum speed setting, and thus the top flow adapter, should be moved. The HCU 54 preferably then directs selective opening of valves 62 to each of the cylinders 36 to provide for the desired piston movement with the hydraulic system while also providing signal to proportional valve 66. Predetermined speed setting could be relative settings such as 100% of voltage or maximum voltage to the valve 66, 25% voltage to the valve, and/or a specific speed setting such as 2 cm/min, etc.

A speed less than maximum speed of plunger 20 can be inputted in the HCU 54 and the HCU receives position information from sensor(s) 60 from which speed can be calculated. The proportional valve 66 can be employed either in the air and/or hydraulic system to selectively vary the flow of hydraulics which moves plunger 20 through movement of pistons 36 at a predetermined speed. By receiving updated information from sensors 60, a feedback loop may be established.

For instance, if a maximum speed of 3 cm/min could be achieved for a given drive system, the controller could provide for the selection of a speed of 3 or less, such as 2 cm/min. The HCU 54 would receive signal input from signals 60 and output a control signal to proportional valve 66. The proportional valve 66 may open or close until the 2 cm/min set point is reached and then possibly continue to hunt.

In addition to pre-setting a speed, speed zones for given elevation ranges could be provided through use of a presently preferred embodiment. For instance, if a column has an operational height of 78 inches, fluid filled to 74 inches, and a resin bed starting at 20 inches, it may be desirable to select 100% speed above 75 inches, then 75% speed to 74 inches, 25% speed to 22 inches and 10% speed to 19 inches. At 19 inches, a bottom limit stop may be reached which could be set at any value at or above a mechanical stop. Accordingly, it may be possible to start downward movement at the first speed and automatically change speeds, in this instance to slower speed at 75 inches and then again automatically change speeds at 74 inches, etc. In this example, the height or elevation at an end of a speed zone is a preset condition identified by the controller 34 with signals provided to the proportional valve 66 to change the speeds. Any of the numbers in this paragraph including speeds and distances could be set at any value desired by the user and may be expressed differently. Percentages have been found effective as they can represent voltage provided to the proportional valve and may not equate directly to a percentage of maximum speed, but to valve parameters.

Alternatively, predetermined speed settings could be provided for in each of the zones in a more direct approach such as by inputting distance/time. The height of specific zones can be selected by the operator in the preferred embodiment. 100% speed may allow for movement when the operator knows the plunger 20 is not in contact with fluid. A slower speed may be desirable as the plunger approaches the fluid. Contacting the fluid and continuing to push at full speed may undesirably pack resin for some applications. Accordingly, slowing to 75% as the fluid is approached is helpful, especially since most columns 10 are stainless steel and thus not transparent to see when contact is made visually. When the operator thinks the fluid will be contacted, a speed of 50% may be desirable. This may continue until the resin bed itself is approached at which time another speed could be selected, such as 25%.

After slowly going through a specific portion of the resin bed, the HCU 54 may stop further compression with a programmably set bottom limit stop.

Since each of the pistons 36 which control movement of the plunger 20 are equipped with position sensors 60, the output from these sensors 60 received by the HCU 54 can be utilized. The elevation of each of the pistons 36 or other elevation corresponding to each of the lifting units connected to the plunger can be monitored.

The HCU 54 can direct the selective opening and closing of at least some of the valves 62 which are in communication with respective cylinders 34 or other appropriate driver to ensure that the top flow adapter and the plunger 20 remain level within the chromatography cylinder 12. By level, it will be understand that being within a predetermined tolerance range of level will be sufficient, such as within a centimeter for a two meter diameter cylinder 12, or other appropriate first tolerance.

Another advantage of using the improved HCU 54 of the preferred embodiment is the ability to further automate the packing process. The output from one or more pressure sensors 60 which could relate to back pressure on the cylinders 34 and/or pressure within the cavity 22. In the prior art, the HCU could downwardly direct the plunger 20 until reaching a predetermined backpressure as measured from the sensor, and preferably while employing the auto level feature, the HCU could secure downward movement upon reaching the set pressure and/or after a predetermined time after reaching the set pressure. However, instead of securing the downward movement which remains a possibility, slowing or otherwise adjusting the speed may be desirable under certain situations such as a pressure event which could include sensing a predetermined pressure and/or a pressure change such as a change in pressure over a given interval.

Additionally, the HCU 54 can also store pressure information at regular intervals such (time intervals could be set such as every ten seconds) as the piston travels. An average of several recorded values could be stored. This average pressure valve can be a travel pressure and is somewhat created by forcing of fluid through the media at specific speeds. This average value can be compared to the actual pressure value as measured in real time. As fluid is expelled, the piston eventually comes in contact with solid media and the actual pressure can increase against the solid bed resistance. When the actual pressure exceeds the travel pressure by a particular amount, a pressure event could possibly be created thereby triggering a shift to a next speed and/or speed zone.

This feature has been found to assist in preventing spring back off of the media. In some embodiments there is a tendency to have premature compression which could otherwise occur when shifting to a slow speed occurs too soon which could cause somewhat of a tendency for media to expand before restricting the spring back tendency with the piston since the fluid being compressed at a particular speed tends to act to assist in compression. This is preferably avoided with some optimum packs. If waiting to shift to a slower speed occurs too late, further compression in the media could occur prematurely with brute pressure force which could also be undesirable in certain situations. Accordingly, utilizing the controller with pressure events has been desirable at least in some applications.

The HCU may also provide the ability to stop movement of the plunger 20, such as if the operator decided to terminate the automated packing process and/or to move the top flow adapter to a preset height.

The new controller 48 may now be utilized with various columns. The preferred embodiment of the controller 48 can identify the type and/or height of the column to which it is connected. This can be advantageous as different control parameters may be utilized with different sized columns. A PLC (or other computer) within the controller such as HCU, or otherwise, upon connection with a cable 64, senses inputs which can be combined as binary numbers (such as the preset open or closed condition of two switches) to identify cylinder diameter and/or cylinder stroke and/or max bed height, etc. The switches provide inputs to the HCU 54 through cable 64 or otherwise.

While the HCU 54 can provide a plurality of automated features, it is also anticipated that it can provide for manual operation including operation of separate valves 62 to respective cylinders (which was not an option in the prior art). Of course, any and potentially all of the automated features can be selected to be off through use of input such as touchscreen 56.

The HCU preferably includes a PLC which is provided with the controller 48. The PLC used in one operational version is an Allen-Bradley (A-B) MocroLogic 1500 Processor with I/O modules. This PLC monitors and controls the operation of three cylinders that support the plunger. The touchscreen 56 is an A-B PanelView 550. Rockwell Automation Software including RSLogix 500 were utilized to develop the PLC programming, PanelBuilder32 was utilized to develop a graphics interface and RSLink was utilized to communicate downloads to the PLC as well as interface with a PC and the touchscreen 56. Other software and hardware as known in the art could also be utilized including computers with monitors that are provided and may have such improved capabilities of improved data storage and/or other capabilities. Other data storage possibilities such as a USB port could also be provided.

The component parts, such as the drum 18, the cylinder 12, and the base are preferably constructed from stainless steel and/or high nickel alloy and/or acrylic. The drive system may be constructed out of appropriate materials including stainless steel. Three or more legs 76, only two of which are illustrated, are connected to the base 64. The drive cylinders 34 are connected to the rim 70 of the base.

Numerous alternations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A method of operating a chromatography column comprising the steps of:
   providing a cylinder with a plunger connected to a drive system configured to provide first and second plunger speeds, said plunger moveable within a cavity of the cylinder in an operational mode, said drive system having at least one driver operably coupled to the plunger, at least one position sensor sensing a position relative to a position of at least one of the driver and the plunger;
   a controller in communication with the position sensor whereby the plunger initially moving at the first speed is automatically changed from the first speed at a first predetermined elevation corresponding to a position related to at least one of the driver and the plunger to the second speed by the controller; wherein at least one of the first and second speeds is a speed other than maximum speed and stopped and the second speed is slower than the first speed.

2. The method of operating the chromatography column of claim 1 wherein the drive system further comprises a proportional valve and speed of the plunger is changed by providing signals to the proportional valve which changes the speed of the plunger as directed by the controller.

3. The method of operating the chromatography column of claim 2 wherein the controller initiates a signal for maximum voltage to be provided at the first speed to the proportional valve, and less than maximum voltage to be provided at the second speed to the proportional valve.

4. The method of operating the chromatography column of claim 1 further comprising a feedback loop whereby the controller can direct a programmed speed for the plunger as one of the first and second speeds.

5. The method of operating the chromatography column of claim 1 further comprising a first speed zone controlled by the controller, and the first speed is a speed of operation in the speed zone, and upon leaving the speed zone at the first elevation, the second speed is initiated by the controller.

6. The method of operating the chromatography column of claim 5 wherein the first speed zone has an upper elevation and the first elevation is a lower elevation with at least one of the upper and lower elevations programmably input into the controller.

7. The method of operating the chromatography column of claim 5 further comprising a second speed zone adjacent to the first speed zone, and a third speed is provided by the controller upon leaving the second speed zone at a second elevation.

8. The method of operating the chromatography column of claim 1 wherein reaching a programmed elevation setting, the plunger is stopped by the controller prior to reaching a mechanical limit.

9. A method of operating a chromatography column comprising the steps of:
   providing a cylinder with a plunger connected to a drive system, said plunger moveable within a cavity of the cylinder in an operational mode at least two speeds, first and second speeds, said drive system having at least one driver operably coupled to the plunger, and
   utilizing a controller in communication with the plunger, moving the plunger at a speed other than maximum speed and stopped as directed by the controller as one of the first and second speeds the first and second speeds are programmably input as preset speeds into the controller with the second speed slower than the first speed, the second speed and occurring at a preset elevation selected by an operator at the controller prior to initiating the first speed, said second speed initiated after the first speed.

10. The method of operating the chromatography column of claim 9 wherein the drive system further comprises at least one position sensor sensing a position relative to a position of at least one of the driver and the plunger; and a speed zone ends at a particular elevation sensed by the at least one position sensor whereby the controller automatically changes speeds from the first to the second speed.

11. The method of operating the chromatography column of claim 9 further comprising a feedback loop whereby the controller directs a programmed speed for the plunger as one of the first and second speeds based on input received from at least one sensor.

\* \* \* \* \*